US008573518B2

(12) United States Patent
Rothmann et al.

(10) Patent No.: US 8,573,518 B2
(45) Date of Patent: Nov. 5, 2013

(54) METHOD AND DEVICE FOR BREAKING DOWN BIOLOGICAL MATERIAL

(75) Inventors: Thomas Rothmann, Langenfeld (DE); Claudia Schmid, Essen (DE); Andreas Schafer, Leverkusen-Schlebusch (DE); Gabriele Christoffel, Cologne (DE)

(73) Assignee: QIAGEN, GmbH, Hilden (DE)

( * ) Notice: Subject to any disclaimer, the term of this patent is extended or adjusted under 35 U.S.C. 154(b) by 389 days.

(21) Appl. No.: 12/989,569

(22) PCT Filed: Apr. 24, 2009

(86) PCT No.: PCT/EP2009/054948
§ 371 (c)(1),
(2), (4) Date: Dec. 21, 2010

(87) PCT Pub. No.: WO2009/130300
PCT Pub. Date: Oct. 29, 2009

(65) Prior Publication Data
US 2011/0101136 A1    May 5, 2011

(30) Foreign Application Priority Data
Apr. 25, 2008    (DE) .................. 10 2008 021 000

(51) Int. Cl.
*B02C 19/00*    (2006.01)
*B02C 11/00*    (2006.01)
(52) U.S. Cl.
USPC .................. 241/1; 241/2; 241/21; 241/23

(58) Field of Classification Search
USPC ................................ 241/1, 2, 21, 23
See application file for complete search history.

(56) References Cited

U.S. PATENT DOCUMENTS

| | | | | |
|---|---|---|---|---|
| 5,074,474 A * | 12/1991 | Golz et al. | ........ | 241/1 |
| 5,918,819 A * | 7/1999 | Rabinovich et al. | ........ | 241/5 |
| 6,699,711 B1 * | 3/2004 | Hahn et al. | ........ | 435/283.1 |
| 6,719,449 B1 | 4/2004 | Laugharn et al. | | |
| 6,739,531 B2 * | 5/2004 | Taylor | ........ | 241/1 |
| 6,878,540 B2 | 4/2005 | Pourahmadi et al. | | |
| 6,881,541 B2 | 4/2005 | Petersen et al. | | |
| 6,887,693 B2 | 5/2005 | McMillan et al. | | |
| 2001/0012612 A1 | 8/2001 | Petersen et al. | | |
| 2002/0039783 A1 | 4/2002 | McMillan et al. | | |
| 2002/0066812 A1 * | 6/2002 | Gazeau | ........ | 241/66 |
| 2004/0200909 A1 * | 10/2004 | McMillan et al. | ........ | 241/1 |
| 2005/0031499 A1 * | 2/2005 | Meier | ........ | 422/128 |
| 2006/0019379 A1 | 1/2006 | Taylor et al. | | |
| 2006/0027686 A1 * | 2/2006 | Taylor et al. | ........ | 241/2 |
| 2006/0030038 A1 * | 2/2006 | Taylor et al. | ........ | 435/306.1 |

FOREIGN PATENT DOCUMENTS

| | | |
|---|---|---|
| CN | 101233910 | 8/2008 |
| EP | 0353365 | 2/1990 |
| EP | 1664264 | 6/2006 |

* cited by examiner

*Primary Examiner* — Faye Francis
(74) *Attorney, Agent, or Firm* — Fanelli Haag & Kilger PLLC

(57) ABSTRACT

The invention relates to a method for breaking down biological material, especially for obtaining biomolecules by ultrasound, the biological material being arranged, in a container together with a liquid.

5 Claims, 3 Drawing Sheets

METHOD AND DEVICE FOR BREAKING DOWN BIOLOGICAL MATERIAL

The invention relates to a method for breaking down biological material, in particular for obtaining biomolecules, by means of ultrasound, the biological material being arranged in a container together with a liquid, and to a device for this purpose.

Methods of this type, such as, for example, the use of ultrasound for breaking down materials such as, for example, organic or inorganic sample material or fossil material, are known from the prior art. In this case, breaking down is performed in order to obtain target constituents of the material to be broken down. The breakdown is performed here in order to obtain target constituents of the material to be broken down. A distinction is made between open and closed environmental parameters during breakdown. In this case breakdown in a closed vessel (see U.S. Pat. No. 6,100,084, for example) can be entirely relevant, since it is possible thereby to achieve a breakdown free from contamination that is, in particular, advantageous for breaking down biological material. The material to be broken down is located in this case in a liquid in the vessel and ultrasound is applied to it.

A disadvantage of breakdown by means of ultrasound in a closed vessel is that the breakdown material can move freely in the liquid. Consequently, the material is either located at a focal point of the ultrasound and is broken down, or not. Furthermore, it is very difficult to influence the degree of breakdown.

U.S. Pat. Nos. 6,878,540, 6,881,541, 6,887,693 and US-A-20060019379 likewise disclose the use of ultrasound to break down material. Use is made as a transducer of an ultrasonic horn that is docked directly onto the wall of the container. In addition, there are added to the liquid in the vessel small spheres that are intended to effect a better breakdown of the material. Furthermore, it is disclosed to pressurize the vessel, which has a flexible wall section, in order to improve the connection between the vessel and transducer and thus to optimize the transition of the sound waves into the vessel. The described methods are, however, complicated and cost-intensive and are successful only under certain conditions.

U.S. Pat. No. 6,719,449 likewise discloses a device and a method for breaking down samples by means of contactless treatment by ultrasound, in the case of which a focused energy beam is used. The sizes of the sample holder are selected in this case to be such that the entire contents are located at the focal point. It is therefore possible to break down only slight amounts of material. Furthermore, the time during which the sample is subjected to ultrasound has to be monitored in order not to insonate excessively.

It is the object of the invention to overcome as far as possible the disadvantages previously mentioned, and to effect a defined breakdown of the breakdown material.

This object is achieved with regard to the method by virtue of the fact that the biological material can move freely in the container, that the biological material is moved by means of centrifugal force to a predetermined point of the container, and that ultrasonic waves are generated during the centrifugation, the ultrasonic waves being focused at a point that is identical to the concentration point, the force resulting at the focus and caused by the ultrasound acting in opposition to the centrifugal force.

The effect of the inventive device is that the material to be broken down is present, owing to the centrifugal force, in a concentrated fashion at a prescribed point in the container that substantially corresponds to the concentration point. The material to be broken down can in this case be organic and/or inorganic sample material such as, for example, fossil or biological material. Furthermore, the material can be present in one piece, for example, in the form of tissue material, or consist of a plurality of individual constituents. Preferably, the material to be broken down can be biological material such as tissue, cells, spores etc., which is suitable, in particular, for obtaining biomolecules, such as cell constituents, proteins, lipids, carbohydrates, nucleic acids etc.

Since both the ultrasonic force and the centrifugal force are set such that they oppose one another with regard to the direction of action, the effect of this is that after a sufficient breakdown of the material the force component of the centrifugal force that acts on the smaller, insoluble particles of the material to be broken down, which are located at the focal point, decreases, and these parts migrate from the focal point, with the effect being firstly to reduce the action of the ultrasonic force on these particles, and then terminate it completely. Thus, furthermore, the result of the breakdown is advantageously, to simultaneously separate from the material that has not been broken down not only the broken down material passing directly into solution (preferably the biomolecules to be obtained), but also the broken down material that is insoluble or has not passed over directly into the solution, the particular consequence being to reduce the time required in bringing about the complete breakdown. The material that has been broken down is preferably small soluble and/or insoluble constituents of the breakdown, with particular preference biomolecules.

Material that has not been, or cannot be, broken down (the cell debris etc., for example in the case of biological material) in this case forms a pellet in the fashion advantageously influenced by the centrifugal force, and remains therein.

An advantageous teaching of the invention provides that the strength of the centrifugal force is set as a function of the particle size of the biological material intended to be broken down. In this way, it is possible to set the breakdown profiles as a function of the material to be broken down, and of the desired degree of breakdown.

A further advantageous teaching of the invention provides that the ultrasonic waves are produced by means of an ultrasonic emitter which preferably is arranged directly in the region of the focus of the predetermined point of the container. A direct emission can thereby be performed. Furthermore, the connection between the emitter and container is improved by the centrifugal force.

A further advantageous design of the inventive method is that the container and/or the liquid are/is cooled. This prevents a change in the material because of the heat produced by the ultrasound in the case of specific breakdown materials, in particular biological materials.

Furthermore, the inventive object is achieved by a device for executing the inventive method having a receptacle for a container, a rotation device for exerting a centrifugal force on the container, and an ultrasonic emitter that is arranged in the region of the container.

The inventive device effects the implementation of the inventive method by machine in a simple way.

A further advantageous teaching of the invention provides that the ultrasonic emitter is arranged in the direction of the centrifugal force. It is thereby possible to direct the ultrasonic force against the acting centrifugal force in a simple way.

The invention is explained in more detail below with the aid of an exemplary embodiment and of a drawing in which:

FIG. 1 to FIG. 5 show the sequence of the inventive method.

Figure 1:
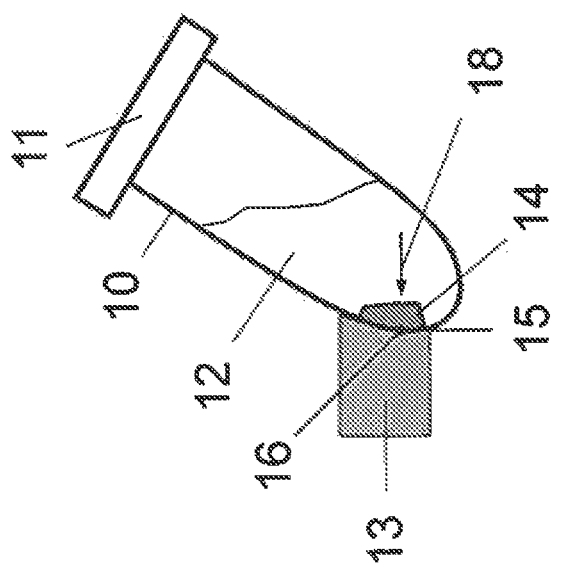
FIG. 1 shows a side view of a container with liquid and breakdown material.
Figure 2:
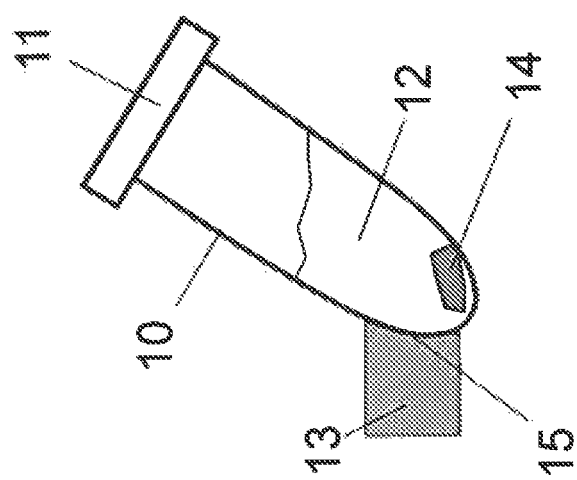
FIG. 2 shows a side view relating to FIG. 1 during the centrifugation.
Figure 3:
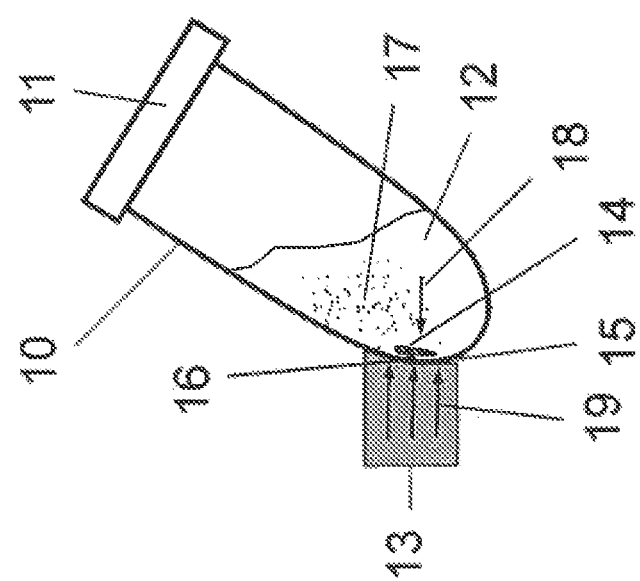
FIG. 3 shows a side view relating to FIG. 2 with the application of ultrasound.

Illustrated in FIG. 1 is a container 10 that is closed by a lid 11. Located in the container 10 are a liquid 12 and, therein, a material 14 to be broken down. An ultrasonic emitter 13 is arranged on a wall section 15 of the container 10. The container 10 is located in a device (not illustrated) that is used to generate a centrifugal force 18 directed outward, as illustrated in FIGS. 2 and 3. The effect of the centrifugal force 18 is that the material 14 to be broken down is arranged at a focal point 16 on the wall section 15. The material 14 to be broken down bunches up at the focal point 16. Furthermore, the ultrasonic waves produced by the emitter 13 also bunch up here (see FIG. 3), and so the ultrasonic force 19 is developed here to the extent of breakdown of the material 14 to be broken down. At the same time, the constituents of the material 14 to be broken down that cannot be broken down or are insoluble are formed in a fashion conditioned by the centrifugal force into a pellet 20, which is deposited and/or remains chiefly in the liquid 12 at the edge of the container 10, in the region of the wall section 15.

Figure 4:
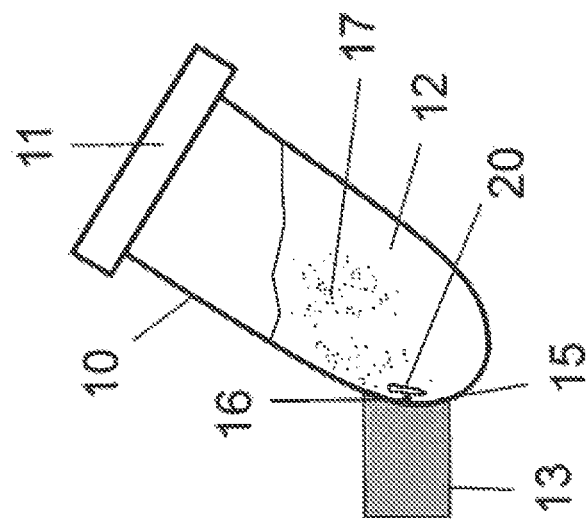
FIG. 4 shows a side view relating to FIG. 1 with broken down material.

FIG. 4 shows the container 10 after the breakdown has been carried out. The broken down material 17, which has passed into solution or has not been kept at the focal point 16 owing to the loss in weight of the individual particles is located in the liquid 12 in a dissolved and/or particulate form. The pellet 20 is located on the wall section 15 or in its vicinity.

Figure 5:
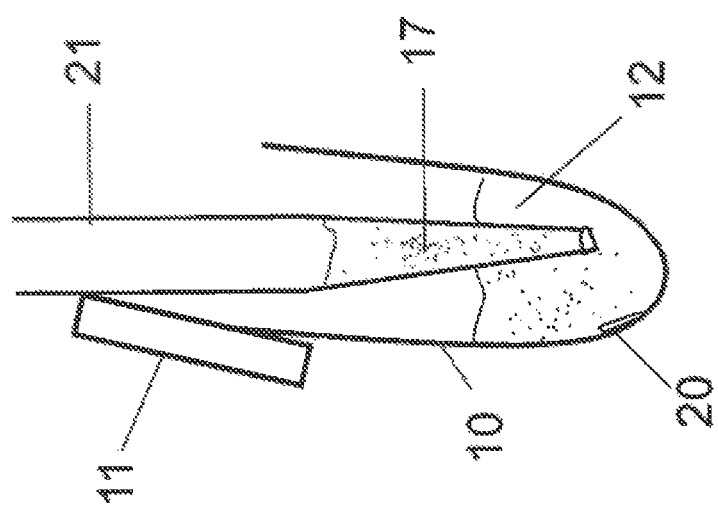
FIG. 5 shows a side view relating to FIG. 4 during the extraction of the broken down material.

FIG. 5 shows the extraction of the material 17 that has been broken down from the container 10 by means of an extraction device 21 such as, for example, a pipette.

LIST OF REFERENCE NUMERALS

10 Container
11 Lid
12 Liquid
13 Emitter
14 Material to be broken down
15 Wall section
16 Focal point
17 Material to be broken down
18 Centrifugal force
19 Ultrasonic force
20 Pellet of the constituents that cannot be broken down
21 Extraction device

The invention claimed is:

1. A method for breaking down biological material to obtain biomolecules, the method comprising:
   a) providing a container comprising a liquid and a biological material to be broken down;
   b) generating a centrifugal force on the biological material to arrange the biological material at a focal point on a wall section of the container; and
   c) generating an ultrasonic wave during the generating the centrifugal force, wherein the ultrasonic wave is focused at the focal point on the wall section of the container, and wherein an ultrasonic force from the ultrasonic wave is in opposition to the centrifugal force, thereby breaking down the biological material to obtain the biomolecules.

2. The method of claim 1 wherein a strength of the centrifugal force is set as a function of particle size of the biological material.

3. The method of claim 1, where the ultrasonic wave is produced by an ultrasonic emitter arranged on the wall section of the container.

4. The method of claim 1, wherein the container and/or the liquid are/is cooled.

5. The method of claim 1, further comprising:
   d) extracting the biomolecules from the liquid.

* * * * *